United States Patent
Muehlberg et al.

(10) Patent No.: US 11,626,203 B2
(45) Date of Patent: Apr. 11, 2023

(54) METHOD AND DATA PROCESSING SYSTEM FOR PROVIDING A PREDICTION OF A MEDICAL TARGET VARIABLE

(71) Applicant: Siemens Healthcare GmbH, Erlangen (DE)

(72) Inventors: Alexander Muehlberg, Nuremberg (DE); Alexander Katzmann, Langensendelbach (DE); Felix Durlak, Langenzenn (DE); Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 195 days.

(21) Appl. No.: 17/009,954

(22) Filed: Sep. 2, 2020

(65) Prior Publication Data

US 2021/0082569 A1 Mar. 18, 2021

(30) Foreign Application Priority Data

Sep. 13, 2019 (EP) .................................... 19197243

(51) Int. Cl.
*G16H 30/40* (2018.01)
*G16H 50/30* (2018.01)
(Continued)

(52) U.S. Cl.
CPC ........... *G16H 30/40* (2018.01); *G06T 7/0012* (2013.01); *G16H 50/20* (2018.01); *G16H 50/30* (2018.01);
(Continued)

(58) Field of Classification Search
None
See application file for complete search history.

(56) References Cited

U.S. PATENT DOCUMENTS

2020/0085382 A1 3/2020 Taerum et al.

FOREIGN PATENT DOCUMENTS

| CN | 101061483 B | * | 1/2013 | ............. G16H 50/20 |
| WO | WO-03079004 A2 | * | 9/2003 | ........... G06F 19/321 |

(Continued)

OTHER PUBLICATIONS

Katzmann, Alexander et al. "Predicting Lesion Growth and Patient Survival in Colorectal Cancer Patients using Deep Neural Networks" 1st Conference on Medical Imaging with Deep Learning (MIDL 2018), Apr. 11, 2018 (Year: 2018).*

(Continued)

*Primary Examiner* — Vu Le
*Assistant Examiner* — Courtney Joan Nelson
(74) *Attorney, Agent, or Firm* — Harness, Dickey & Pierce, P.L.C.

(57) ABSTRACT

In one embodiment, a computer-implemented method provides a prediction of a medical target variable. The computer-implemented method includes receiving medical imaging data of an examination area, the examination area including a plurality of lesions of an anatomical structure, wherein each lesion of the plurality of lesions of the anatomical structure spaced apart from any other lesion of the plurality of lesions of the anatomical structure; calculating a spread parameter based on the medical imaging data, the spread parameter being indicative of a spread of a spatial distribution of the plurality of lesions of the anatomical structure; calculating the prediction of the medical target variable based on the spread parameter; and providing the prediction of the medical target variable.

18 Claims, 8 Drawing Sheets

(51) Int. Cl.
  *G16H 50/20* (2018.01)
  *G06T 7/00* (2017.01)
(52) U.S. Cl.
  CPC ............... *G06T 2207/20081* (2013.01); *G06T 2207/30056* (2013.01); *G06T 2207/30096* (2013.01)

(56) References Cited

FOREIGN PATENT DOCUMENTS

| WO | WO-2006119340 A2 * | 11/2006 | ........... G06T 7/0012 |
|----|----|----|----|
| WO | WO 2018222755 A1 | 12/2018 | |

OTHER PUBLICATIONS

Swanson, Kristin R., et al. "Virtual and Real Brain Tumors: Using Mathematical Modeling to Quantify Glioma Growth and Invasion." Journal of the Neurological Sciences, vol. 216, No. 1, 2003, pp. 1-10., https://doi.org/10.1016/j.jns.2003.06.001. (Year: 2003).*

Machine translation of CN-101061483-B (Year: 2013).*

Katzmann, Alexander et al. "TumorEncode—Deep Convolutional Autoencoder for Computed Tomography Tumor Treatment Assessment" 2018 International Joint Conference on Neural Networks (IJCNN), IEEE, Jul. 8, 2018 (Jul. 8, 2018).

Katzmann, Alexander et al. "Predicting Lesion Growth and Patient Survival in Colorectal Cancer Patients using Deep Neural Networks" 1st Conference on Medical Imaging with Deep Learning (MIDL 2018), Apr. 11, 2018 (Apr. 11, 2018).

Dabass, Manju et al. "Review of Classification Techniques Using Deep Learning for Colorectal Cancer Imaging Modalities" 2019 6th International Conference on Signal Processing and Integrated Networks (SPIN), IEEE, pp. 105-110, Mar. 2019 (Mar. 7, 2019).

Etchebehere, Elba C. et al. "Prognostic Factors in Patients Treated with 223Ra: The Role of Skeletal Tumor Burden on Baseline 18F-Fluoride PET/CT in Predicting Overall Survival" Journal of Nuclear Medicine, vol. 56, No. 8, pp. 1177-1184, 2015.

Extended European Search Report for European Application No. 19197243.9 dated Feb. 20, 2020.

* cited by examiner

METHOD AND DATA PROCESSING SYSTEM FOR PROVIDING A PREDICTION OF A MEDICAL TARGET VARIABLE

PRIORITY STATEMENT

The present application hereby claims priority under 35 U.S.C. § 119 to European patent application number EP 19197243.9 filed Sep. 13, 2019, the entire contents of which are hereby incorporated herein by reference.

FIELD

Various examples of embodiments of the invention relate to a computer-implemented method for providing a prediction of a medical target variable; to a method for providing a trained machine learning algorithm; to a data processing system; to a computer program product and to a computer-readable medium.

BACKGROUND

Metastatic colorectal cancer (mCRC) is one of the leading causes of cancer related deaths in modern societies. An adequate and early assessment is systematically correlated with a significantly improved overall patient survival and patient wellbeing. Within tumor therapy, the approximated patient survival itself is an important variable for therapy adjustment, e.g. by adapting the medication, or escalating and deescalating the therapy. Thus, it contributes to an overall better patient care and patient survival. However, currently there is no established and generally accepted technique to quantitatively estimate patient survival, meaning that this estimation largely builds up on radiologic and oncologic experience. The potential of a simple, easily measurable and quantifiable biomarker to estimate the patient survival is therefore of high clinical, as well as business value, as this method could establish a new standard within oncologic therapies.

The survival of patients can be estimated based on features like volume or maximum diameter of single, or the sum of these values for multiple lesions (Response Evaluation Criteria in Solid Tumors—RECIST).

SUMMARY

While the currently researched automated inference of features through deep convolutional neural networks (DCNNs) is a generally promising alternative to the above mentioned handcrafted features, the inventors have discovered that a major problem arises from the required network capacity, and therefore parameter amount, to train deep learning models, as there is a lack of large and easily available medical datasets for this purpose.

The inventors have discovered that an underlying technical problem of the invention is to facilitate an improved quantitative assessment of lesions of an anatomical structure in respect of their relevance for a medical target variable. At least one embodiment of the invention and the subject matter of at least one of the claims, is to improve upon or even solve this problem. The claims are related to further aspects and embodiments of the invention.

In one embodiment, the invention relates to a computer-implemented method for providing a prediction of a medical target variable, the method comprising:
 receiving medical imaging data of an examination area, the examination area comprising a plurality of lesions of an anatomical structure, wherein each lesion of the plurality of lesions of the anatomical structure spaced apart from any other lesion of the plurality of lesions of the anatomical structure;
 calculating a spread parameter based on the medical imaging data, the spread parameter being indicative of a spread of a spatial distribution of the plurality of lesions of the anatomical structure;
 calculating the prediction of the medical target variable based on the spread parameter; and
 providing the prediction of the medical target variable.

In another embodiment, the invention relates to a computer-implemented method for providing a trained machine learning algorithm, comprising:
 receiving a plurality of training datasets, each training dataset of the plurality of training datasets comprising
  respective training medical imaging data of an examination area, the examination area comprising a respective plurality of lesions of an anatomical structure, wherein each lesion of the respective plurality of lesions of the anatomical structure is spaced apart from any other lesion of the respective plurality of lesions of the anatomical structure,
  a respective label spread parameter, the label spread parameter being indicative of a spread of a spatial distribution of the respective plurality of lesions of the anatomical structure,
  a respective label of a medical target variable;
 training a machine learning algorithm based on the plurality of training datasets, the training comprising a first optimization of the machine learning algorithm for calculating a spread parameter and a second optimization of the machine learning algorithm for calculating a prediction of a medical target variable,
 wherein the first optimization for calculating the spread parameter is based on at least a first part of the plurality of training datasets, in particular on the plurality of training datasets,
 wherein the second optimization for calculating the prediction of the medical target variable is based on at least a second part of the plurality of training datasets, in particular on the plurality of training datasets; and
 providing the trained machine learning algorithm.

In another embodiment, the invention relates to a data processing system for providing a prediction of a medical target variable, the data processing system comprising
 a medical imaging data receiver for receiving medical imaging data of an examination area, the examination area comprising a plurality of lesions of an anatomical structure, wherein each lesion of the plurality of lesions of the anatomical structure is spaced apart from any other lesion of the plurality of lesions of the anatomical structure;
 a spread parameter calculator for calculating a spread parameter based on the medical imaging data, the spread parameter being indicative of a spread of a spatial distribution of the plurality of lesions of the anatomical structure;
 a prediction calculator for calculating the prediction of the medical target variable based on the spread parameter; and
 a prediction provider for providing the prediction of the medical target variable.

In another embodiment the data processing system is configured to implement the method according to one or more of the disclosed embodiments.

In one embodiment, the invention relates to a medical imaging device comprising a data processing system for providing a prediction of a medical target variable according to one or more of the disclosed embodiments. The medical imaging device may be, for example, a computed tomography (CT) device or a magnetic resonance imaging (MRI) device or a combination of different medical imaging modalities, for example, a PET-CT-imaging device. The medical imaging data can be acquired, for example, by the medical imaging device. The medical imaging data can comprise, for example, computed tomography medical imaging data and/or magnetic resonance medical imaging data.

In another embodiment, the invention relates to a computer program product comprising program elements which induce a data processing system to carry out the steps of the method according to one or more of the disclosed embodiments, when the program elements are loaded into a memory of the data processing system.

In another embodiment, the invention relates to a computer-readable medium on which program elements are stored that can be read and executed by a data processing system, in order to perform the steps of the method according to one or more of the disclosed embodiments, when the program elements are executed by the data processing system.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable medium can be embodied as non-permanent main memory (e.g. random-access memory) or as permanent mass storage (e.g. hard disk, USB stick, SD card, solid state disk).

In another embodiment, the invention relates to a computer-implemented method for providing a prediction of a medical target variable, the method comprising:

receiving medical imaging data of an examination area, the examination area including a plurality of lesions of an anatomical structure, each lesion of the plurality of lesions of the anatomical structure being spaced apart from any other lesion of the plurality of lesions of the anatomical structure;

calculating a spread parameter based on the medical imaging data received, the spread parameter being indicative of a spread of a spatial distribution of the plurality of lesions of the anatomical structure;

calculating the prediction of the medical target variable based on the spread parameter calculated; and providing the prediction of the medical target variable, calculated.

In another embodiment, the invention relates to a computer-implemented method for providing a trained machine learning algorithm, comprising:

receiving a plurality of training datasets, each respective training dataset of the plurality of training datasets comprising respective training medical imaging data of an examination area, the examination area including a plurality of lesions of an anatomical structure, wherein each lesion of the plurality of lesions of the anatomical structure is spaced apart from any other lesion of the plurality of lesions of the anatomical structure, a respective label spread parameter, the respective label spread parameter being indicative of a spread of a spatial distribution of the plurality of lesions of the anatomical structure, a respective label of a medical target variable;

training a machine learning algorithm based on the plurality of training datasets, the training comprising a first optimization of the machine learning algorithm for calculating a spread parameter and a second optimization of the machine learning algorithm for calculating a prediction of a medical target variable, wherein the first optimization for calculating the spread parameter is based on at least a first part of the plurality of training datasets, wherein the second optimization for calculating the prediction of the medical target variable is based on at least a second part of the plurality of training datasets and providing the machine learning algorithm trained.

In another embodiment, the invention relates to a data processing system for providing a prediction of a medical target variable, comprising:

a medical imaging data receiver to receive medical imaging data of an examination area, the examination area including a plurality of lesions of an anatomical structure, wherein each lesion of the plurality of lesions of the anatomical structure is spaced apart from any other lesion of the plurality of lesions of the anatomical structure;

a spread parameter calculator to calculate a spread parameter based on the medical imaging data received, the spread parameter being indicative of a spread of a spatial distribution of the plurality of lesions of the anatomical structure;

a prediction calculator to calculate the prediction of the medical target variable based on the spread parameter; and a prediction provider to provide the prediction of the medical target variable calculated.

In another embodiment, the invention relates to a non-transitory computer program product storing program elements, to induce a data processing system to carry out the method of an embodiment, when the program elements are loaded into a memory of the data processing system and executed by the data processing system.

In another embodiment, the invention relates to a non-transitory computer-readable medium storing program elements, readable and executable by a data processing system, to perform the method of an embodiment, when the program elements are executed by the data processing system.

BRIEF DESCRIPTION OF THE DRAWINGS

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

Figure 1:
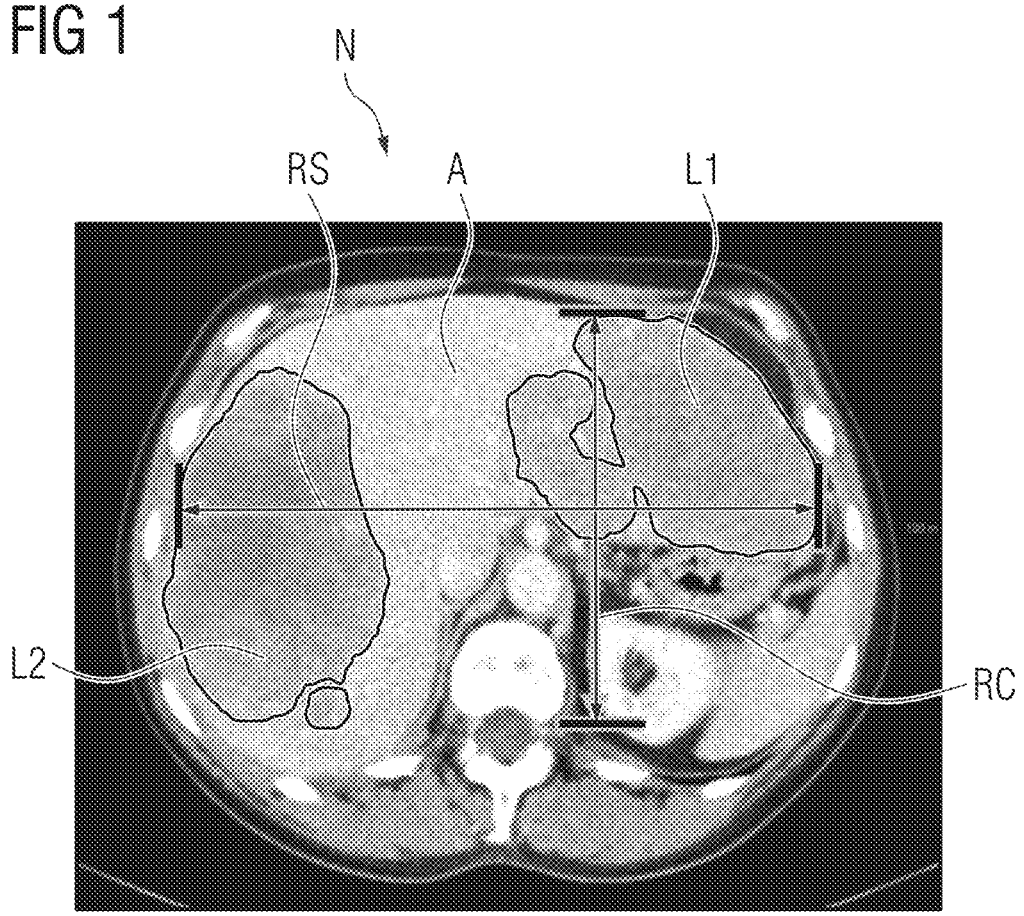
FIG. 1 shows a medical image of an anatomical structure with a first example of a plurality of lesions in an axial reformation.

The above and other elements, features, steps, and concepts of the present disclosure will be more apparent from the following detailed description in accordance with example embodiments of the invention, which will be explained with reference to the accompanying drawings.

Some examples of the present disclosure generally provide for a plurality of circuits, data storages, connections, or electrical devices such as e.g. processors. All references to these entities, or other electrical devices, or the functionality provided by each, are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

It is to be understood that the following description of embodiments is not to be taken in a limiting sense. The scope of the invention is not intended to be limited by the embodiments described hereinafter or by the drawings, which are taken to be illustrative only.

The drawings are to be regarded as being schematic representations, and elements illustrated in the drawings are not necessarily shown to scale. Rather, the various elements are represented such that their function and general purpose become apparent to a person skilled in the art. Any connection, or communication, or coupling between functional blocks, devices, components, or other physical or functional units shown in the drawings or described herein may also be implemented by an indirect connection or coupling. A communication between devices may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment, the invention relates to a computer-implemented method for providing a prediction of a medical target variable, the method comprising:

receiving medical imaging data of an examination area, the examination area comprising a plurality of lesions of an anatomical structure, wherein each lesion of the plurality of lesions of the anatomical structure spaced apart from any other lesion of the plurality of lesions of the anatomical structure;

calculating a spread parameter based on the medical imaging data, the spread parameter being indicative of a spread of a spatial distribution of the plurality of lesions of the anatomical structure;

calculating the prediction of the medical target variable based on the spread parameter; and providing the prediction of the medical target variable.

In another embodiment, each lesion of the plurality of lesions of the anatomical structure is related to a same disease as any other lesion of the plurality of lesions of the anatomical structure. In another aspect, each lesion of the plurality of lesions of the anatomical structure is of a same tissue and/or a same type as any other lesion of the plurality of lesions of the anatomical structure. The plurality of lesions of the anatomical structure can comprise, for example, two or three or more than three lesions of the anatomical structure.

The anatomical structure can comprise, for example, at least one further lesion that is not comprised in the plurality of lesions. The plurality of lesions can comprise, for example, an entire tumor burden of the anatomical structure.

The medical imaging data can comprise, for example, a respective representation for each of the lesions of the plurality of lesions. For each of the lesions of the plurality of lesions the respective representation can be obtained, for example, based on segmentation, in particular automated and/or manual segmentation. In another aspect, for each lesion of the plurality of lesions a respective volume is determined based on the respective representation. The prediction of the medical target variable can be further based on a volume parameter, that is calculated based on the respective volumes of the lesions of the plurality of lesions.

In another embodiment, a trained machine learning algorithm is applied onto the medical imaging data, thereby obtaining the spread parameter and/or the prediction of the medical target variable. The trained machine learning algorithm can be, for example, a trained deep convolutional neural network.

In another embodiment, the trained machine learning algorithm is based on a first optimization for calculating the spread parameter and/or a second optimization for calculating the prediction of the medical target variable. The first optimization for calculating the spread parameter can be based on at least a first part of a plurality of training datasets, in particular on the plurality of training datasets. The second optimization for calculating the prediction of the medical target variable can be based on at least a second part of the plurality of training datasets, in particular on the plurality of training datasets.

In another embodiment, the second optimization for calculating the prediction of the medical target variable is separate from and/or subsequent to the first optimization for calculating the spread parameter.

In another embodiment, the trained machine learning algorithm is based on multi-task learning, the multi-task learning comprising the first optimization and the second optimization as related tasks, in particular related tasks that are simultaneously solved.

The first optimization for calculating the spread parameter can be based on a first loss, for example a reconstruction loss. The second optimization for calculating the prediction of the medical target variable can be based on a second loss, for example a discriminative loss. The multi-task learning can comprise a weighting, in particular an automated weighting, of the first loss and the second loss relative to each other. The weighting can be based, for example, on a homoscedastic task uncertainty.

In another embodiment, the calculating the spread parameter comprises determining a first spread of the spatial distribution of the plurality of lesions of the anatomical structure with respect to a first direction, determining a second spread of the spatial distribution of the plurality of lesions of the anatomical structure with respect to a second direction, the second direction being orthogonal to the first direction, and determining a third spread of the spatial distribution of the plurality of lesions of the anatomical structure with respect to a third direction, the third direction being orthogonal to the first direction and the second direction. The spread parameter can be calculated based on the first spread, the second spread and the third spread.

The first direction can be, for example, a sagittal direction. The second direction can be, for example, a coronal direction. The third direction can be, for example, an axial direction.

A spread of a spatial distribution with respect to a given direction can be, for example, a maximum extension of the spatial distribution along that given direction and/or a maximum extension of a convex envelope of the spatial distribution along that given direction. In another aspect effective extensions are used instead of maximum extensions, for example to smoothen or eliminate the impact of outlier lesions onto the spread parameter.

In another embodiment, an envelope, in particular a convex envelope, of the spatial distribution can be determined. The first direction can be, for example, parallel to a first principal axis of the convex envelope. The second direction can be, for example, parallel to a second principal axis of the convex envelope. The third direction can be, for example, parallel to a third principal axis of the convex envelope. Thereby the spread parameter can be obtained in a rotational invariant form.

In another embodiment, the spread parameter can be a function of the first spread, the second spread and the third spread, each of the first spread, the second spread and the third spread being an input of the function. In another aspect, the spread parameter can be a function of a ratio of the first spread to the first diameter of the anatomical structure, a ratio of the second spread to the second diameter of the anatomical structure and a ratio of the third spread to the third diameter of the anatomical structure. The function can be, for example, a non-linear function, in particular, a random forest-based function and/or a function that is implemented in form of a set of weights of a deep convolutional neural network.

The spread parameter can be, for example, a real number or a tuple of real numbers. The tuple can be, in particular, a 3-tuple comprising a first element based on the first spread, for example the ratio of the first spread to the first diameter of the anatomical structure, a second element based on the second spread, for example the ratio of the second spread to the second diameter of the anatomical structure, and a third element based on the third spread, for example the ratio of the third spread to the third diameter of the anatomical structure.

In another embodiment, the prediction of the medical target variable is a function of the spread parameter, in particular of the spread parameter in form of a tuple, each element of the tuple being an input of the function of the spread parameter. The function of the spread parameter can be, for example, a non-linear function of the spread parameter, in particular, a random forest-based function of the spread parameter and/or a function of the spread parameter that is implemented in form of a set of weights of a deep convolutional neural network.

In another embodiment, the spread parameter is calculated based on a generalized mean of the first spread, the second spread and the third spread. The generalized mean can be, for example, an arithmetic mean or a quadratic mean. The generalized mean can be, for example, a weighted generalized mean or an unweighted generalized mean.

In the context of embodiments of the present disclosure, it is understood that if for calculating the spread parameter a function of the first spread, the second spread and the third spread is used that equals a result of multiplying a non-zero constant and a generalized mean of the first spread, the second spread and the third spread, the spread parameter is calculated based on said generalized mean of the first spread, the second spread and the third spread.

For example, if the spread parameter is a sum of the first spread, the second spread and the third spread and/or a function of the sum of the first spread, the second spread and the third spread, then for calculating the spread parameter an function of the first spread, the second spread and the third spread is used that equals a result of multiplying the non-zero constant having the value three and the arithmetic mean of the first spread, the second spread and the third spread, and therefore the spread parameter is calculated based on the arithmetic mean of the first spread, the second spread and the third spread. In particular, the sum of the first spread, the second spread and the third spread can be understood as an inner function and the function of the sum can be understood as an outer function.

In another embodiment, the spread parameter is calculated based on a sum of the first spread, the second spread and the third spread. The spread parameter can be, for example, a sum or a generalized mean, in particular an arithmetic mean or a quadratic mean, of the first spread, the second spread and the third spread.

A sum or a generalized mean of the first spread, the second spread and the third spread can be used as a label spread parameter for the training of the machine learning algorithm. This example feature may be refined in the first optimization of the machine learning algorithm for calculating the spread parameter, for example, in a deep learning procedure.

In another embodiment, each of a first diameter of the anatomical structure with respect to the first direction, a second diameter of the anatomical structure with respect to the second direction and a third diameter of the anatomical structure with respect to the third direction is determined.

The spread parameter can be calculated based on a ratio of the first spread to the first diameter of the anatomical structure, a ratio of the second spread to the second diameter of the anatomical structure and a ratio of the third spread to the third diameter of the anatomical structure.

The spread parameter can be, for example, a sum or a generalized mean of a ratio of the first spread to the first diameter of the anatomical structure, a ratio of the second spread to the second diameter of the anatomical structure and a ratio of the third spread to the third diameter of the anatomical structure. Thereby the spread parameter can be normalized with respect to the size of the anatomical structure.

A sum or a generalized mean of a ratio of the first spread to the first diameter of the anatomical structure, a ratio of the second spread to the second diameter of the anatomical structure and a ratio of the third spread to the third diameter of the anatomical structure can be used as a label spread parameter for the training of the machine learning algorithm. This example feature may be refined in the first optimization of the machine learning algorithm for calculating the spread parameter, for example, in a deep learning procedure.

In another embodiment, the anatomical structure comprises at least one organ, in particular is at least one organ. In another aspect each lesion of the plurality of lesions of the anatomical structure is related to a tumor of the at least one organ. The examination area can be, for example, an examination area of a patient. The at least one organ can be, for example, at least one organ of the patient.

In another embodiment, the at least one organ is selected from the organ group consisting of a liver, a lung, a brain and a kidney. The plurality of lesions of the anatomical structure can be, for example, a plurality of lung nodules of the lung.

In another embodiment, the anatomical structure comprises a lymphatic system, in particular is a lymphatic system. The plurality of lesions of the anatomical structure can be, for example, a plurality of enlarged lymph nodes of the lymphatic system.

In another embodiment, the medical target variable is selected from the medical target variable group consisting of a survival estimation, a therapy response estimation and a therapy recommendation. The survival estimation can be, for example, a one-year survival estimation and/or a five-year survival estimation. The therapy recommendation can be indicative, for example, of a best suited therapy with respect to the anatomical structure.

In another embodiment, the anatomical structure is a liver, each lesion of the plurality of lesions of the anatomical structure is related to a tumor of the liver, and the medical target variable is a survival estimation.

In another embodiment, the invention relates to a computer-implemented method for providing a trained machine learning algorithm, comprising:

receiving a plurality of training datasets, each training dataset of the plurality of training datasets comprising
  respective training medical imaging data of an examination area, the examination area comprising a respective plurality of lesions of an anatomical structure, wherein each lesion of the respective plurality of lesions of the anatomical structure is spaced apart from any other lesion of the respective plurality of lesions of the anatomical structure,
  a respective label spread parameter, the label spread parameter being indicative of a spread of a spatial distribution of the respective plurality of lesions of the anatomical structure,
  a respective label of a medical target variable;
training a machine learning algorithm based on the plurality of training datasets, the training comprising a first optimization of the machine learning algorithm for calculating a spread parameter and a second optimization of the machine learning algorithm for calculating a prediction of a medical target variable,
wherein the first optimization for calculating the spread parameter is based on at least a first part of the plurality of training datasets, in particular on the plurality of training datasets,
wherein the second optimization for calculating the prediction of the medical target variable is based on at least a second part of the plurality of training datasets, in particular on the plurality of training datasets; and
providing the trained machine learning algorithm.

The first part of the plurality of training datasets can comprise, for each training dataset of the plurality of training datasets, the respective training medical imaging data and the respective label spread parameter. The second part of the plurality of training datasets can comprise, for each training dataset of the plurality of training datasets, the respective label spread parameter and the respective label of the medical target variable.

The training medical imaging data can comprise, for example, a respective representation for each of the lesions of the respective plurality of lesions. For each of the lesions of the respective plurality of lesions the respective representation can be obtained, for example, based on segmentation, in particular automated segmentation and/or manual segmentation.

In another embodiment, for each training dataset of the plurality of training datasets the respective training medical imaging data of the examination area is of the same physical dimensions, for example, in millimeters, as the respective training medical imaging data of any other training dataset of the plurality of training datasets. Thereby consistent physical distances among the training datasets can be preserved. In particular, for each training dataset of the plurality of training datasets the respective training medical imaging data can be resized, for example be cut, if necessary, to match a pre-defined physical size.

For the training, 2.5D reformations, i.e., slices of a fixed size, which focus on the center-of-mass of the respective plurality of lesions and/or show all lesions of the anatomical structure for example in axial, coronal and/or sagittal orientation can be used as training medical imaging data.

In another embodiment, the machine learning algorithm is trained based on multi-task learning, the multi-task learning comprising the first optimization and the second optimization as related tasks. The multi-task learning can comprise, in particular, a simultaneous solving of the first optimization and the second optimization as related tasks.

In another embodiment, for each training dataset of the plurality of training datasets the respective label spread parameter is of a same spread feature class as the respective label spread parameter of any other training dataset of the plurality of training datasets. The spread feature class can be determined according to one or more aspects disclosed with respect to the spread parameter.

Thereby a search space of the machine learning algorithm can be constraint to focus on the entire spatial distribution of the plurality of lesions and not on single lesion features like shape and texture, in particular to solutions that are similar to a spread parameter.

A decision-support system based on the trained machine learning algorithm according to one or more of the disclosed embodiments might facilitate an easily understandable and interpretable decision. A reformation of the medical imaging data for use in the training of the machine learning algorithm, for example in form of a deep convolutional neural network, may be adjusted, leading to a machine learning algorithm which uses physical distances and/or tumor spread for prediction.

For each training dataset of the plurality of training datasets the respective label of the medical target variable can be determined according to one or more aspects disclosed with respect to the label of the medical target variable.

In another embodiment, the invention relates to a data processing system for providing a prediction of a medical target variable, the data processing system comprising a medical imaging data receiver for receiving medical imaging data of an examination area, the examination area comprising a plurality of lesions of an anatomical structure, wherein each lesion of the plurality of lesions of the anatomical structure is spaced apart from any other lesion of the plurality of lesions of the anatomical structure;

a spread parameter calculator for calculating a spread parameter based on the medical imaging data, the spread parameter being indicative of a spread of a spatial distribution of the plurality of lesions of the anatomical structure;

a prediction calculator for calculating the prediction of the medical target variable based on the spread parameter; and a prediction provider for providing the prediction of the medical target variable.

In another embodiment the data processing system is configured to implement the method according to one or more of the disclosed embodiments.

In one embodiment, the invention relates to a medical imaging device comprising a data processing system for providing a prediction of a medical target variable according to one or more of the disclosed embodiments. The medical imaging device may be, for example, a computed tomography (CT) device or a magnetic resonance imaging (MRI) device or a combination of different medical imaging modalities, for example, a PET-CT-imaging device. The medical imaging data can be acquired, for example, by the medical imaging device. The medical imaging data can comprise, for example, computed tomography medical imaging data and/or magnetic resonance medical imaging data.

In another embodiment, the invention relates to a computer program product comprising program elements which induce a data processing system to carry out the steps of the method according to one or more of the disclosed embodiments, when the program elements are loaded into a memory of the data processing system.

In another embodiment, the invention relates to a computer-readable medium on which program elements are stored that can be read and executed by a data processing system, in order to perform the steps of the method according to one or more of the disclosed embodiments, when the program elements are executed by the data processing system.

The computer program product can be, for example, a computer program or comprise another element apart from the computer program. This other element can be hardware, for example a memory device, on which the computer program is stored, a hardware key for using the computer program and the like, and/or software, for example, a documentation or a software key for using the computer program. A computer-readable medium can be embodied as non-permanent main memory (e.g. random-access memory) or as permanent mass storage (e.g. hard disk, USB stick, SD card, solid state disk).

The data processing system can comprise, for example, at least one of a cloud-computing system, a distributed computing system, a computer network, a computer, a tablet computer, a smartphone or the like. The data processing system can comprise hardware and/or software. The hardware can be, for example, a processor system, a memory system and combinations thereof. The hardware can be configurable by the software and/or be operable by the software. Calculations for performing a step of a method and/or for training a machine learning algorithm may be carried out in a processor.

Data, in particular the medical imaging data and the training datasets, can be received, for example, by receiving a signal that carries the data and/or by reading the data from a computer-readable medium and/or by receiving an input through a user interface. Data, in particular, the spread parameter and the prediction of the medical target variable can be provided, for example, by transmitting a signal that carries the data and/or by writing the data into a computer-readable medium and/or by displaying the data on a display.

Wherever not already described explicitly, individual embodiments, or their individual aspects and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

Any of the algorithms mentioned herein can be based on one or more of the following architectures: convolutional neural network, deep belief network, random forest, deep residual learning, deep reinforcement learning, recurrent neural network, Siamese network, generative adversarial network or auto-encoder. In particular, the trained machine learning algorithm can be embodied as a deep learning algorithm, in particular as a deep convolutional neural network.

In the context of the present invention, the expression "based on" can in particular be understood as meaning "using, inter alia". In particular, wording according to which a first feature is calculated (or generated, determined etc.) based on a second feature does not preclude the possibility of the first feature being calculated (or generated, determined etc.) based on a third feature.

For example, the prediction of the medical target variable can be calculated based on the spread parameter and further based on at least one additional feature. The at least one additional feature can be related to the plurality of lesions, for example, being indicative of a volume, for example a total combined volume and/or a mean volume, of the lesions of the plurality of lesions. The at least one additional feature can be related to patient parameters like age, sex or weight of the patient.

Reference is made to the fact that the described methods and the described units are merely preferred example embodiments of the invention and that the invention can be varied by a person skilled in the art, without departing from the scope of the invention as it is specified by the claims.

Figure 2:
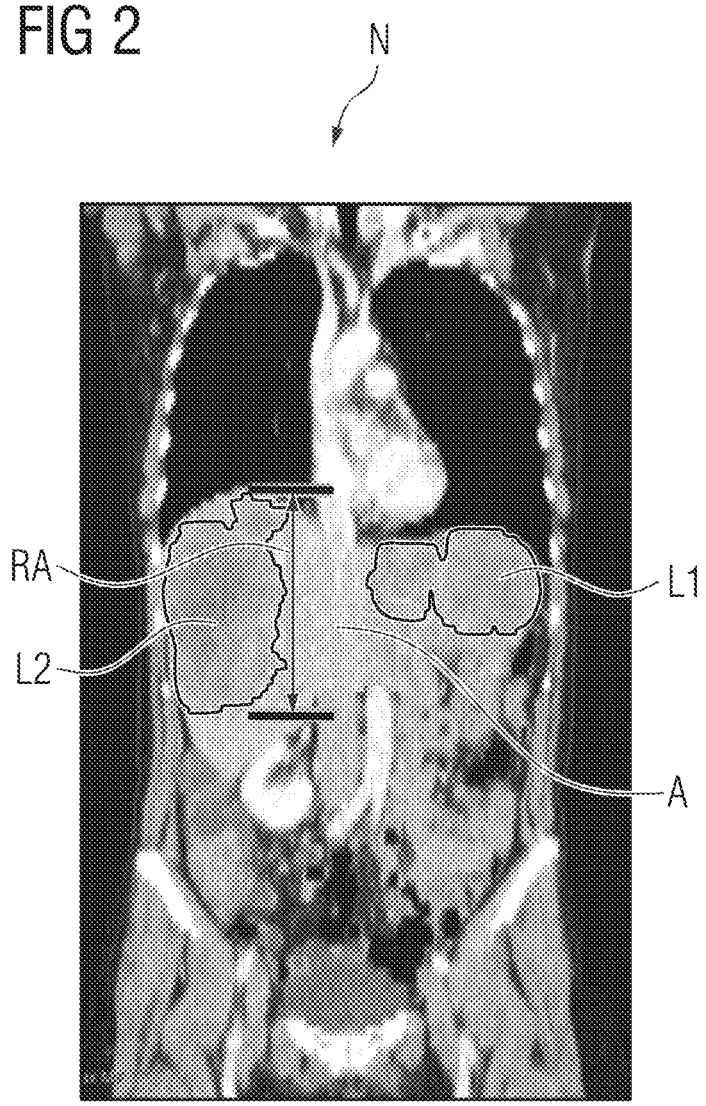
FIG. 2 shows a medical image of the anatomical structure with the first example of a plurality of lesions in a coronal reformation.

FIG. 1 shows a medical image of an anatomical structure A with a first example of a plurality of lesions L1, L2 in an axial reformation. FIG. 2 shows a medical image of the anatomical structure A with the first example of a plurality of lesions L1, L2 in a coronal reformation.

Figure 3:
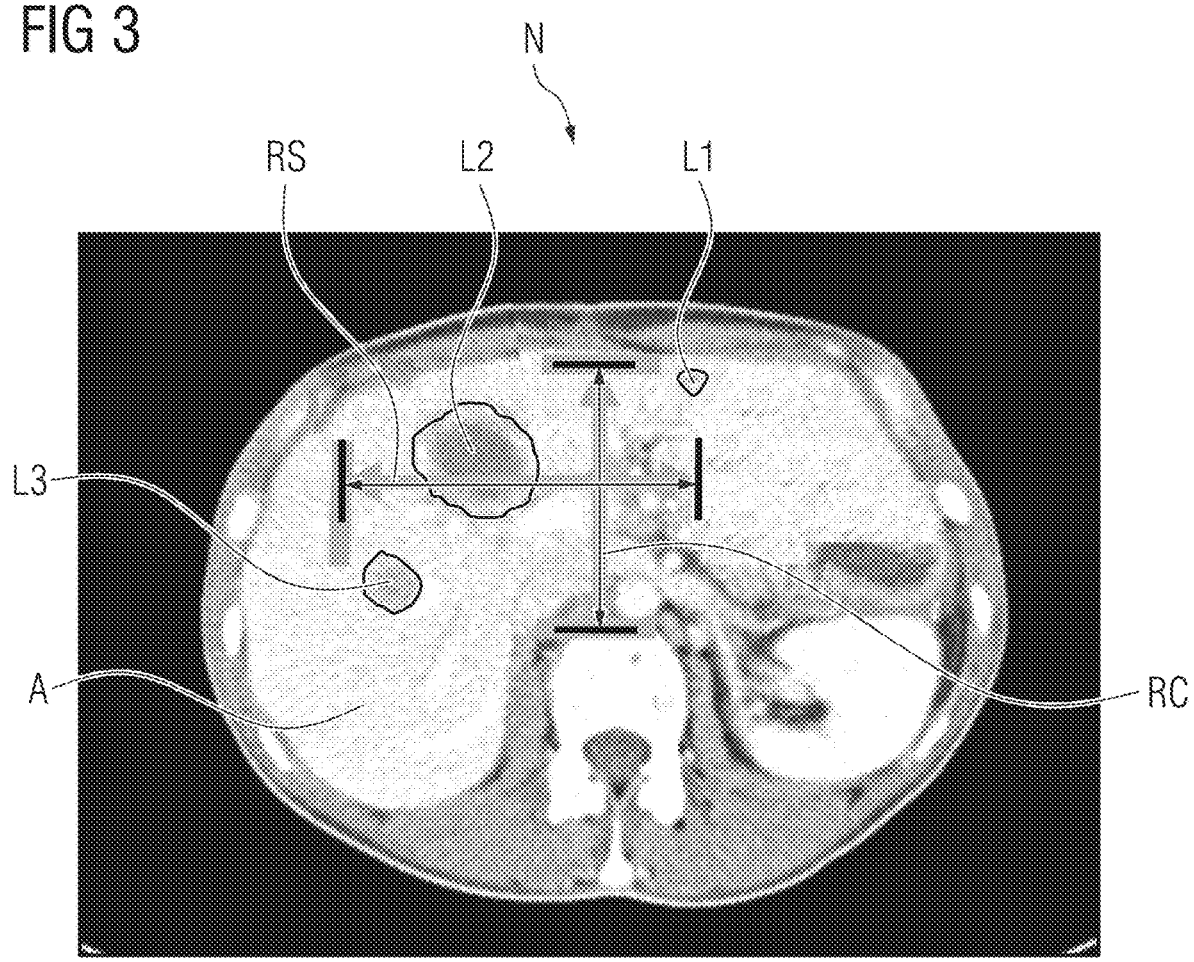
FIG. 3 shows a medical image of an anatomical structure with a second example of a plurality of lesions in an axial reformation.
Figure 4:
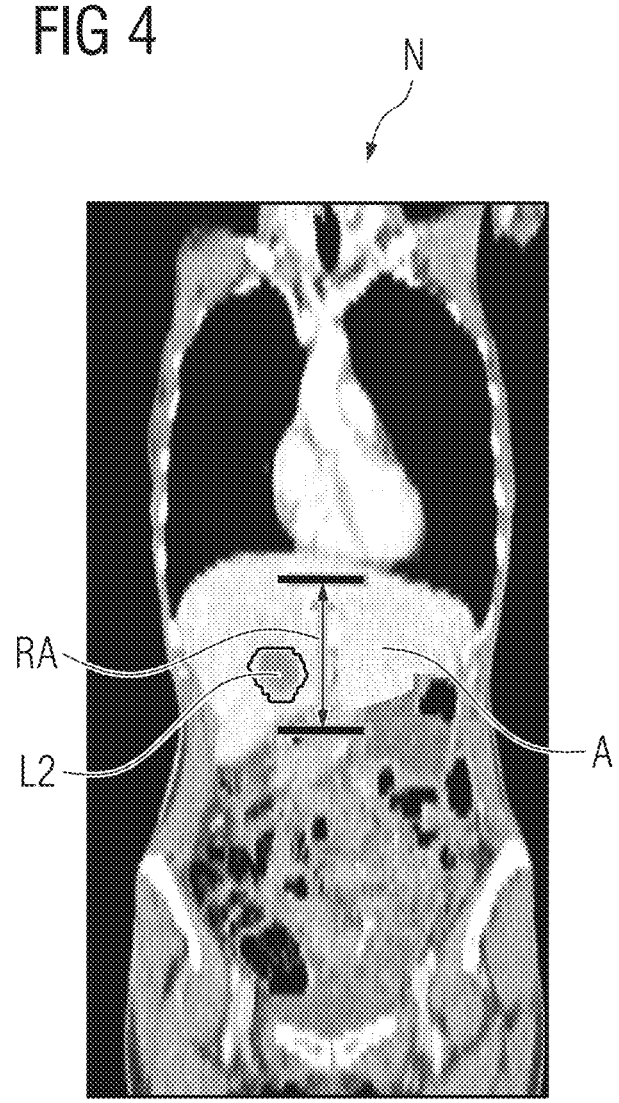
FIG. 4 shows a medical image of the anatomical structure with the second example of a plurality of lesions in a coronal reformation.

FIG. 3 shows a medical image of an anatomical structure A with a second example of a plurality of lesions L1, L2, L3 in an axial reformation. FIG. 4 shows a medical image of the anatomical structure with the second example of a plurality of lesions L1, L2, L3 in a coronal reformation.

Figure 5:
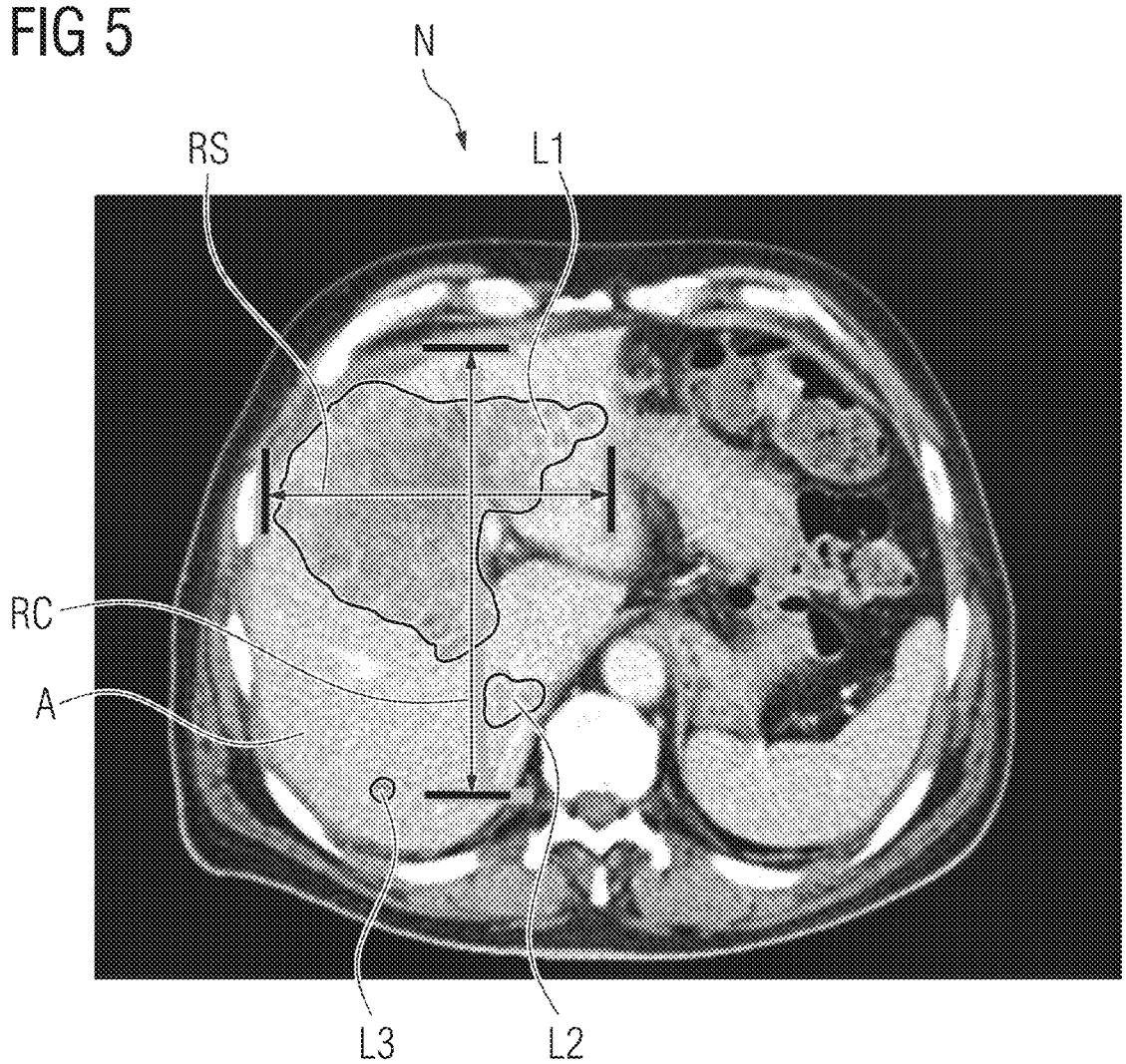
FIG. 5 shows a medical image of an anatomical structure with a third example of a plurality of lesions in an axial reformation.
Figure 6:
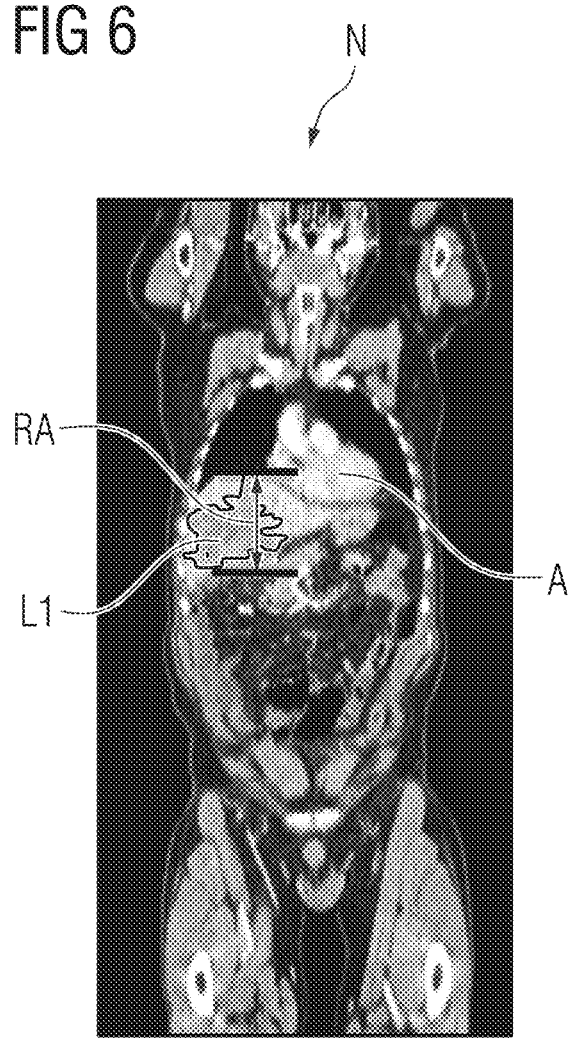
FIG. 6 shows a medical image of the anatomical structure with the third example of a plurality of lesions in a coronal reformation.

FIG. 5 shows a medical image of an anatomical structure A with a third example of a plurality of lesions L1, L2, L3 in an axial reformation. FIG. 6 shows a medical image of the anatomical structure A with the third example of a plurality of lesions L1, L2, L3 in a coronal reformation, The dimension line RS represents a first spread of the spatial distribution of the plurality of lesions L1, L2, L3 of the anatomical structure A with respect to a first direction, the first direction being a sagittal direction. The dimension line RC represents a second spread of the spatial distribution of the plurality of lesions L1, L2, L3 of the anatomical structure A with respect to a second direction, the second direction being a coronal direction. The dimension line RA represents a third spread of the spatial distribution of the plurality of lesions L1, L2, L3 of the anatomical structure A with respect to a third direction, the third direction being an axial direction.

The spread parameter can be calculated based on the first spread, the second spread and the third spread. Based on the spread parameter, a prediction of a medical target variable can be calculated, for example to predict the death and/or survival probability of the patient for one year.

The spread parameter F3DATS quantifies the maximum tumor spread for the three anatomical orientations axial, sagittal and coronal within an organ. Therefore, the spread parameter F3DATS could be named "3D anatomical tumor spread". This spread parameter is measured in the physical unit millimeters (mm).

The spread parameter F3DATS can be the sum of the first spread $r_{sagittal}$, the second spread $r_{coronal}$ and the third spread $r_{axial}$. Then the mathematical formulation for the feature $F_{3DATS}$ can be given by: $F_{3DATS}[mm]=(r_{max,\,axial}-r_{min,\,axial})+(r_{max,\,sagittal}-r_{min,\,sagittal})+(r_{max,\,coronal}-r_{min,\,coronal})=r_{axial}+r_{sagittal}+r_{coronal}$. In another example, the spread parameter $F_{3DATS\_NL}$ can be a non-linear function, for example a random forest-based function, of the first spread $r_{sagittal}$, the second spread $r_{coronal}$ and the third spread $r_{axial}$ as inputs of the non-linear function, $F_{3DATS\_NL}[mm]=f(r_{axial},\,r_{sagittal},\,r_{coronal})$ These features are intuitively easy to understand and interpretable. Furthermore, a deep dispersion feature for a quantification of a spatial distribution of the plurality of lesions can be constructed, which can be pre-trained, for example, by a handcrafted dispersion feature F3DATS. When predicting one-year-survival for oncology patients, superior performance can be achieved based on F3DATS when compared to complex radiomics features, the RECIST diameter as well as the overall tumor volume.

In an example clinical study (103 samples) for one-year-survival prediction based on the entire tumor burden of the liver, a prediction based on F3DATS resulted in an ROC AUC (Area Under the Receiver Operating Characteristics Curve) of 71%, whereas a prediction based on the RECIST diameter resulted in an ROC AUC of 56%, a prediction based on the tumor volume resulted in an ROC AUC of 56% and a prediction based on radiomics features resulted in an ROC AUC of 62%.

The measured quantities and relevant images can be displayed to a physician on a screen and/or within a graphical user interface, thereby facilitating a quantitative assessment of the lesions of the anatomical structure A in respect of their relevance for the medical target variable.

The displayed information can comprise, for each of the first spread $r_{sagittal}$, the second spread $r_{coronal}$, the third spread $r_{axial}$ and the resulting $F_{3DATS}$, a respective numerical value, in particular in millimeters (mm). The numerical values can be related, for example, to anatomical distances or to distances measured in the medical images.

In the case shown in FIG. 5 and FIG. 6, the following values can be displayed:
154 mm for the first spread $r_{sagittal}$,
140 mm for the second spread $r_{coronal}$,
98 mm for the third spread $r_{axial}$,
392 mm for $F_{3DTAS}$,
0.68 for a ratio of the first spread $r_{sagittal}$ to a first diameter of the anatomical structure A with respect to the first direction,
0.8 for a ratio of the second spread $r_{coronal}$ to the second diameter of the anatomical structure A with respect to the second direction,
0.59 for a ratio of the third spread $r_{axial}$ to the third diameter of the anatomical structure A with respect to the third direction,
0.68 for a mean ratio, and
68% for a probability for death of the patient within one year, which is calculated in a manner as explained above.

Figure 7:
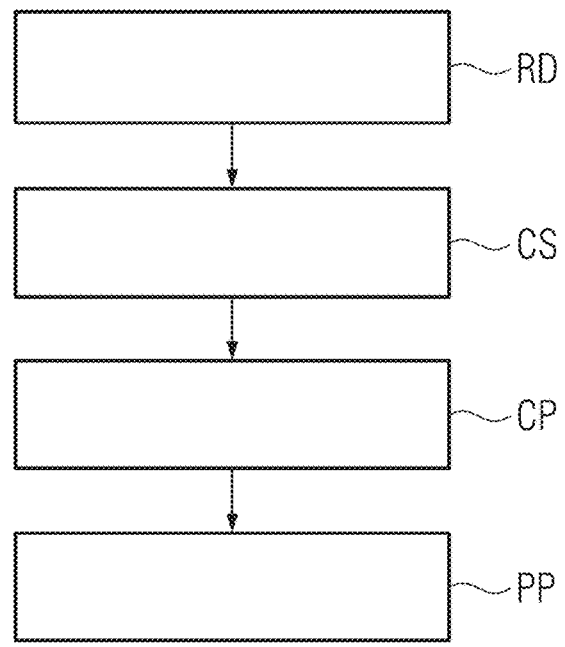
FIG. 7 shows a diagram illustrating a computer-implemented method for providing a prediction of a medical target variable.

FIG. 7 shows a diagram illustrating a computer-implemented method for providing a prediction of a medical target variable, the method comprising
receiving RD medical imaging data of an examination area N, the examination area N comprising a plurality of lesions L1, L2, L3 of an anatomical structure A, wherein each lesion of the plurality of lesions L1, L2, L3 of the anatomical structure A is spaced apart from any other lesion of the plurality of lesions L1, L2, L3 of the anatomical structure A, calculating CS a spread parameter based on the medical imaging data, the spread parameter being indicative of a spread of a spatial distribution of the plurality of lesions L1, L2, L3 of the anatomical structure A, calculating CP the prediction of the medical target variable based on the spread parameter, and providing PP the prediction of the medical target variable.

Figure 8:
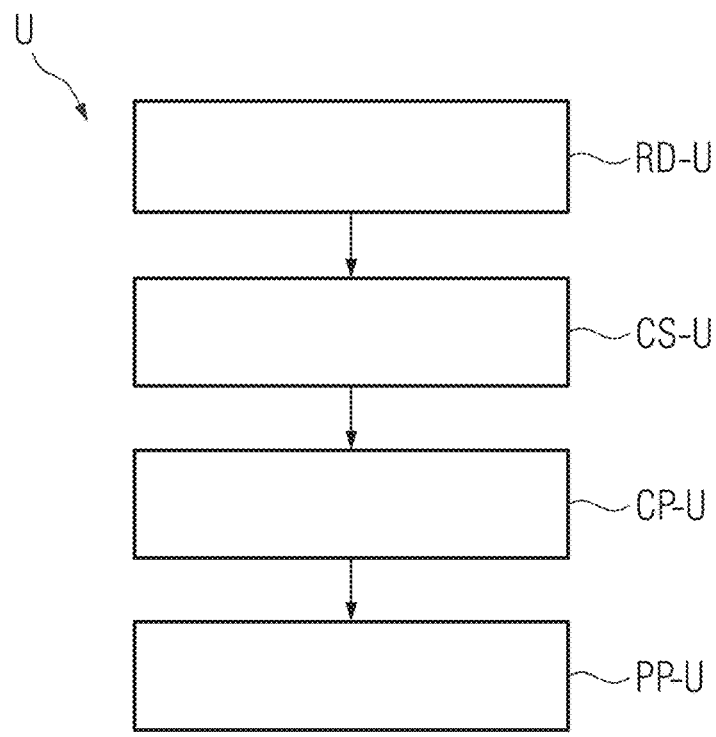
FIG. 8 shows a data processing system for providing a prediction of a medical target variable.

FIG. 8 shows a data processing system U for providing a prediction of a medical target variable, and the data processing system U comprising:

a medical imaging data receiver RD-U for receiving RD medical imaging data of an examination area N, the examination area N comprising a plurality of lesions L1, L2, L3 of an anatomical structure A, wherein each lesion of the plurality of lesions L1, L2, L3 of the anatomical structure A is spaced apart from any other lesion of the plurality of lesions L1, L2, L3 of the anatomical structure A, a spread parameter calculator CS-U for calculating CS a spread parameter based on the medical imaging data, the spread parameter being indicative of a spread of a spatial distribution of the plurality of lesions L1, L2, L3 of the anatomical structure A, a prediction calculator CP-U for calculating CP the prediction of the medical target variable based on the spread parameter, and a prediction provider PP-U for providing PP the prediction of the medical target variable.

Figure 9:
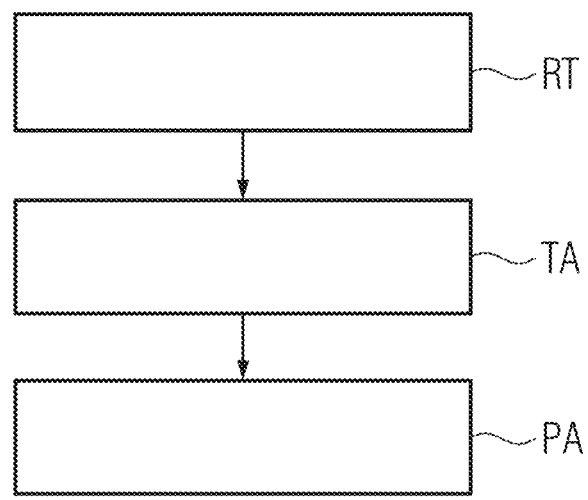
FIG. 9 shows a diagram illustrating a computer-implemented method for providing a trained machine learning algorithm.

FIG. 9 shows a diagram illustrating a computer-implemented method for providing a trained machine learning algorithm, the method comprising:

receiving RT a plurality of training datasets, each training dataset of the plurality of training datasets comprising:

respective training medical imaging data of an examination area N, the examination area N comprising a plurality of lesions L1, L2, L3 of an anatomical structure A, wherein each lesion of the plurality of lesions L1, L2, L3 of the anatomical structure A is spaced apart from any other lesion of the plurality of lesions L1, L2, L3 of the anatomical structure A, a respective label spread parameter, the label spread parameter being indicative of a spread of a spatial distribution of the plurality of lesions L1, L2, L3 of the anatomical structure A, a respective label of a medical target variable, training TA a machine learning algorithm based on the plurality of training datasets, the training comprising a first optimization of the machine learning algorithm for calculating a spread parameter and a second optimization of the machine learning algorithm for calculating a prediction of a medical target variable;

wherein the first optimization for calculating the spread parameter is based on at least a first part of the plurality of training datasets, wherein the second optimization for calculating the prediction of the medical target variable is based on at least a second part of the plurality of training datasets; and providing PA the trained machine learning algorithm.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for providing a prediction of a medical target variable, the method comprising:

obtaining a spread parameter based on medical imaging data of an examination area, the examination area including an anatomical structure having a plurality of lesions, each of the plurality of lesions being spaced apart from each other lesion among the plurality of lesions, and the spread parameter being based on at least a first ratio between a first diameter of the anatomical structure in a first direction and a first maximum distance between a first outer edge of the plurality of lesions and a second outer edge of the plurality of lesions in the first direction;

obtaining the prediction of the medical target variable based on the spread parameter; and providing the prediction of the medical target variable, wherein at least one of the spread parameter or the prediction of the medical target variable are obtained by applying the medical imaging data to a trained machine learning algorithm.

2. The method of claim 1, wherein the trained machine learning algorithm is trained by performing a first training and a second training, the first training including training a first machine learning algorithm to calculate the spread parameter based on at least a first part of a plurality of training datasets, and the second training including training the first machine learning algorithm to calculate the prediction of the medical target variable based on at least a second part of the plurality of training datasets.

3. The method of claim 2, wherein the performing the second training performs the second training subsequent to the first training.

4. The method of claim 2, wherein the trained machine learning algorithm is trained based on multi-task learning, the multi-task learning including the first training and the second training as related tasks.

5. The method of claim 3, wherein the spread parameter is based on
the first ratio,
a second ratio between a second diameter of the anatomical structure in a second direction and a second maximum distance between a third outer edge of the plurality of lesions and a fourth outer edge of the plurality of lesions in the second direction, the second direction being orthogonal to the first direction, and
a third ratio between a third diameter of the anatomical structure in a third direction and a third maximum distance between a fifth outer edge of the plurality of lesions and a sixth outer edge of the plurality of lesions in the third direction, the third direction being orthogonal to the first direction and the second direction.

6. The method of claim 5, wherein the spread parameter is based on a mean of the first ratio, the second ratio, and the third ratio.

7. The method of claim 1, wherein the spread parameter is based on
the first ratio,
a second ratio between a second diameter of the anatomical structure in a second direction and a second maximum distance between a third outer edge of the plurality of lesions and a fourth outer edge of the plurality of lesions in the second direction, the second direction being orthogonal to the first direction, and
a third ratio between a third diameter of the anatomical structure in a third direction and a third maximum distance between a fifth outer edge of the plurality of lesions and a sixth outer edge of the plurality of lesions in the third direction, the third direction being orthogonal to the first direction and the second direction.

8. The method of claim 7, wherein the spread parameter is based on a mean of the first ratio, the second ratio, and the third ratio.

9. A non-transitory computer-readable medium storing program elements that, when executed by a data processing system, cause the data processing system to perform the method of claim 7.

10. The method of claim 1, wherein
the anatomical structure includes at least one organ; and
each of the plurality of lesions corresponds to a tumor of the at least one organ.

11. The method of claim 10, wherein the at least one organ includes a liver, a lung, a brain or a kidney.

12. The method of claim 1, wherein
the anatomical structure includes a lymphatic system; and
the plurality of lesions are a plurality of enlarged lymph nodes of the lymphatic system.

13. The method of claim 1, wherein the medical target variable includes a survival estimation, a therapy response estimation or a therapy recommendation.

14. The method of claim 1, wherein
the anatomical structure is a liver;
each of the plurality of lesions corresponds to a tumor of the liver; and
the medical target variable is a survival estimation.

15. A non-transitory computer-readable medium storing program elements that, when executed by a data processing system, cause the data processing system to carry out the method of claim 1.

16. The method of claim 1, wherein the spread parameter is based on at least two different lesions among the plurality of lesions.

17. A computer-implemented method for providing a trained machine learning algorithm, the method comprising:
receiving a plurality of training datasets, each respective training dataset among the plurality of training datasets including
respective training medical imaging data of a corresponding examination area, the corresponding examination area including an anatomical structure having a plurality of lesions, each of the plurality of lesions being spaced apart from each other lesion among the plurality of lesions,
a respective label spread parameter based on at least a first ratio between a first diameter of the anatomical structure in a first direction and a first maximum distance between a first outer edge of the plurality of lesions and a second outer edge of the plurality of lesions in the first direction, and
a respective label of a medical target variable;
training a machine learning algorithm based on the plurality of training datasets to obtain the trained machine learning algorithm, the training including performing a first training and a second training, the first training including training the machine learning algorithm to calculate a first spread parameter based on at least a first part of the plurality of training datasets, and the second training includes training the machine learning algorithm to calculate a prediction of a first medical target variable based on at least a second part of the plurality of training datasets; and
providing the trained machine learning algorithm.

18. A data processing system to provide a prediction of a medical target variable, the data processing system comprising:
at least one processor configured to execute computer-readable instructions to cause the data processing system to
obtain a spread parameter based on medical imaging data of an examination area, the examination area including an anatomical structure having a plurality of lesions, each of the plurality of lesions being spaced apart from each other lesion among the plurality of lesions, and the spread parameter being based on at least a first ratio between a first diameter of the anatomical structure in a first direction and a first maximum distance between a first outer edge of the plurality of lesions and a second outer edge of the plurality of lesions in the first direction;
obtain the prediction of the medical target variable based on the spread parameter, and
provide the prediction of the medical target variable, wherein
the data processing system is configured to obtain at least one of the spread parameter or the prediction of the medical target variable applying the medical imaging data to a trained machine learning algorithm.

* * * * *